(12) United States Patent
Merce-Vidal et al.

(10) Patent No.: US 7,498,328 B2
(45) Date of Patent: Mar. 3, 2009

(54) DERIVATIVES OF SULPHONAMIDES, THEIR PREPARATION AND USE AS MEDICAMENTS

(75) Inventors: Ramón Merce-Vidal, Barcelona (ES); Blas Andaluz-Mataro, Barcelona (ES); Jordi Frigola-Constansa, Barcelona (ES)

(73) Assignee: Laboratorias Del Dr. Esteve, S.A., Barcelona (ES)

(*) Notice: Subject to any disclaimer, the term of this patent is extended or adjusted under 35 U.S.C. 154(b) by 161 days.

(21) Appl. No.: 11/487,745

(22) Filed: Jul. 17, 2006

(65) Prior Publication Data

US 2006/0258653 A1 Nov. 16, 2006

Related U.S. Application Data

(62) Division of application No. 10/933,951, filed on Sep. 3, 2004, now Pat. No. 7,176,200, which is a division of application No. 10/293,206, filed on Nov. 13, 2002, now Pat. No. 7,105,515.

(30) Foreign Application Priority Data

Nov. 17, 2001 (ES) ............... 200102517

(51) Int. Cl.
| | |
|---|---|
| *A61K 31/5377* | (2006.01) |
| *A61K 31/495* | (2006.01) |
| *A61K 31/404* | (2006.01) |
| *C07D 413/06* | (2006.01) |
| *C07D 209/04* | (2006.01) |

(52) U.S. Cl. ............... 514/235.2; 544/111; 544/373; 546/192; 546/201; 548/465; 548/491; 514/252.13; 514/414

(58) Field of Classification Search .......... 544/111, 544/373; 546/192, 201; 548/465; 514/235.2, 514/252.13, 414

See application file for complete search history.

(56) References Cited

U.S. PATENT DOCUMENTS

| 5,962,473 A | 10/1999 | Johnson et al. |
| 5,962,474 A | 10/1999 | Audia et al. |
| 6,380,201 B1 | 4/2002 | Johnson et al. |
| 7,105,515 B2 * | 9/2006 | Merce-Vidal et al. .... 514/235.2 |
| 7,176,200 B2 * | 2/2007 | Merce-vidal et al. ..... 514/235.2 |

* cited by examiner

*Primary Examiner*—Golam M Shameem
(74) *Attorney, Agent, or Firm*—Katten Muchin Rosenman LLP

(57) ABSTRACT

The present invention relates to new derivatives of sulphonamides, with the general formula (I), as well as to their physiologically acceptable salts, the processes for their preparation, their application as medicaments in human and/or veterinary therapy and the pharmaceutical compositions that contain them.

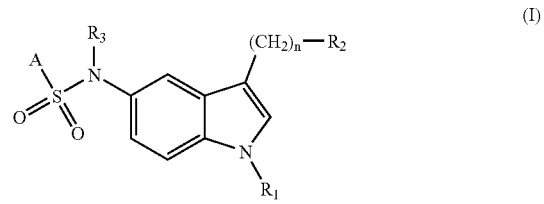

4 Claims, No Drawings

DERIVATIVES OF SULPHONAMIDES, THEIR PREPARATION AND USE AS MEDICAMENTS

CROSS REFERENCE TO RELATED APPLICATION

The present application is a divisional application of U.S. Pat. application Ser. No. 10/933,951 which was filed on Sep. 3, 2004, now U.S. Pat. No. 7,176,200, which is a divisional of allowed U.S. Pat. application Ser. No. 10/293,206 filed Nov. 13, 2002, now U.S. Pat No. 7,105,515 the contents of which are hereby incorporated by reference.

FIELD OF THE INVENTION

The present invention relates to new derivatives of sulphonamides, with the general formula (I), as well as to their physiologically acceptable salts, the processes for their preparation, their application as medicaments in human and/or veterinary therapy and the pharmaceutical compositions that contain them.

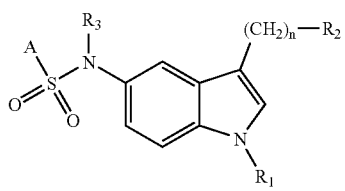

(I)

The new compounds object of the present invention can be used in the pharmaceutical industry as intermediates and for preparing medicaments.

BACKGROUND OF THE INVENTION

The superfamily of serotonin receptors (5-HT) includes 7 classes (5-HT$_1$-5-HT$_7$) encompassing 14 human subclasses [D. Hoyer, et al., *Neuropharmacology*, 1997, 36, 419]. The 5-HT$_6$ receptor is the latest serotonin receptor identified by molecular cloning both in rats [F. J. Monsma, et al., *Mol. Pharmacol.*, 1993, 43, 320; M. Ruat, et al., *Biochem. Biophys. Res. Commun.*, 1993, 193, 268] and in humans [R. Kohen, et al., *J. Neurochem.*, 1996, 66, 47]. Compounds with 5-HT$_6$ receptor antagonistic activity are useful for the treatment of various disorders of the Central Nervous System and of the gastrointestinal tract, such as irritable intestine syndrome. Compounds with 5-HT$_6$ receptor antagonistic activity are useful in the treatment of anxiety, depression and cognitive memory disorders [M. Yoshioka, et al., *Ann. NY Acad. Sci.*, 1998, 861, 244; A. Bourson, et al., *Br. J. Pharmacol.*, 1998, 125, 1562; D. C. Rogers, et al., *Br. J. Pharmacol. Suppl.*, 1999, 127, 22P; A. Bourson, et al., *J. Pharmacol. Exp. Ther.*, 1995, 274, 173; A. J: Sleight, et al., *Behav. Brain Res.*, 1996, 73, 245; T. A. Branchek, et al., *Annu. Rev. Pharmacol. Toxicol.*, 2000, 40, 319; C. Routledge, et al., *Br. J. Pharmacol.*, 2000, 130, 1606]. It has been shown that typical and atypical antipsychotic drugs for treating schizophrenia have a high affinity for 5-HT$_6$ receptors [B. L. Roth, et al., *J. Pharmacol. Exp. Ther.*, 1994, 268, 1403; C. E. Glatt, et al., *Mol. Med.*, 1995, 1, 398; F. J. Mosma, et al., *Mol. Pharmacol.*, 1993, 43, 320; T. Shinkai, et al., *Am. J. Med. Genet.*, 1999, 88, 120]. Compounds with 5-HT$_6$ receptor antagonistic activity are useful for treating infant hyperkinesia (ADHD, attention deficit/hyperactivity disorder) [W. D. Hirst, et al., *Br. J. Pharma-col.*, 2000, 130, 1597; C. Gérard, et al., *Brain Research*, 1997, 746, 207; M. R. Pranzatelli, *Drugs of Today*, 1997, 33, 379]. Patent application WO 01/32646 describes sulphonamides derived of bicycles, with 6 members each, aromatic or heteroaromatic with 5-HT$_6$ receptor antagonistic activity. Patent application EP 0733628 describes sulphonamides derived of indole with an 5-HT$_{1F}$ receptor antagonistic activity useful for treating migraines. In general, the study of the scientific literature and patents indicates that small structural variations give rise to agonist or antagonist compounds of various receptors of serotonin that are useful for treating different diseases, depending on the receptor for which they show affinity.

After laborious research the inventors have managed to synthesize new compounds with the general formula (I) that show interesting biological properties making them particularly useful for use in human and/or veterinary therapy.

DETAILED DESCRIPTION OF THE INVENTION

The present invention provides new compounds with 5-HT$_6$ serotonin receptor antagonistic activity useful in the preparation of a medicament for prevention or treatment of various disorders of the Central Nervous System, and in particular anxiety, depression, cognitive memory disorders and senile dementia or other dementia processes in which there is a predominant cognition deficit, psychosis, infant hyperkinesia (ADHD, attention deficit/hyperactivity disorder) and other disorders mediated by the 5-HT$_6$ serotonin receptor in mammals, including man.

The compounds object of the present invention have the general formula (I)

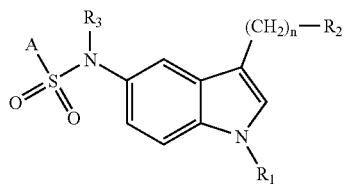

(I)

wherein

A represents a substituent selected from among:
  A heteroaromatic ring of 5 or 6 members containing 1 or 2 heteroatoms selected from among oxygen, nitrogen and sulphur, optionally substituted by 1 or 2 halogen atoms, by a C$_1$-C$_4$ alkyl radical or by a phenyl or heteroaryl radical with 5 or 6 members containing 1 or 2 atoms of oxygen, nitrogen or sulphur:
  A bicyclic heteroaromatic ring containing 1 to 3 heteroatoms selected from among oxygen, nitrogen and sulphur, optionally substituted by 1 or 2 halogen atoms or by a C$_1$-C$_4$ alkyl radical:
  A group selected from among:

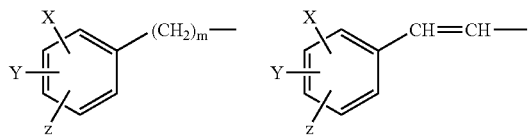

-continued

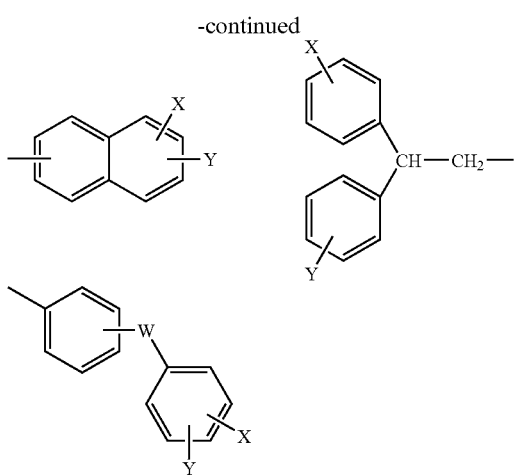

R₁ represents hydrogen, a $C_1$-$C_4$ alkyl radical or a benzyl radical;

n represents 0, 1, 2, 3 or 4;

R₂ represents —NR₄R₅ or a group with formula:

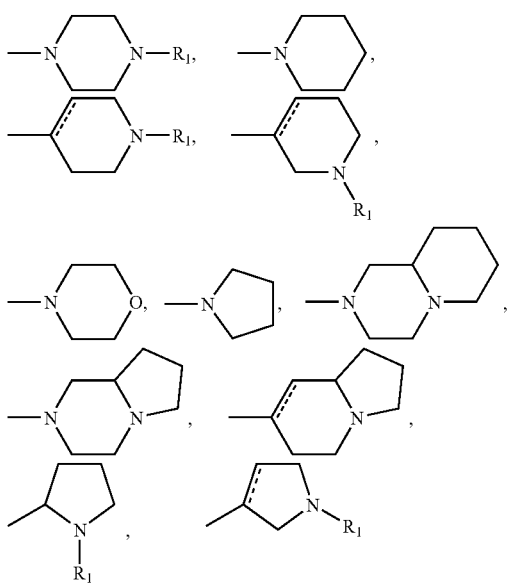

Wherein the dotted line represents an optional chemical bond;

R₃, R₄ y R₅ independently represent hydrogen or a $C_1$-$C_4$ alkyl;

X, Y and Z independently represent hydrogen, fluorine, chlorine, bromine, a $C_1$-$C_4$ alkyl, a $C_1$-$C_4$, alkoxy, a $C_1$-$C_4$ alkylthio, trifluoromethyl, cyano, nitro and —NR₄R₅;

W represents a bond between the two rings, $CH_2$, O, S and NR₄;

m represents 0, 1, 2, 3 or 4:

with the condition that when m=0, A is a substituted phenyl;

or one of its physiologically acceptable salts.

The alkyl term $C_1$-$C_4$ represents a linear or branched carbonated chain including 1 to 4 atoms of carbon, such as methyl, ethyl, propyl, isopropyl, butyl, isobutyl, sec-butyl and terc-butyl.

Compounds object of the present invention that correspond to the above formula can be selected from among:

[1] N-[3-(2-diethylaminoethyl)-1H-indol-5-yl]-5-chloro-3-methylbenzo[b]thiophene-2-sulphonamide.

[2] N-[3-(2-diethylaminoethyl)-1H-indol-5-yl]naphthalene-1-sulphonamide.

[3] Hydrochloride N-[3-(2-diethylaminoethyl)-1H-indol-5-yl]naphthalene-1-sulphonamide.

[4] N-[3-(2-diethylaminoethyl)-1H-indol-5-yl]-3,5-dichlorobenzenesulphonamide.

[5] N-[3-(2-diethylaminoethyl)-1H-indol-5-yl]-4-phenylbenzenesulphonamide.

[6] N-[3-(2-diethylaminoethyl)-1H-indol-5-yl]-5-chlorothiophene-2-sulphonamide.

[7] N-[3-(2-dimethylaminoethyl)-1H-indol-5-yl]-5-chloro-3-methylbenzo[b]thiophene-2-sulphonamide.

[8] N-[3-(2-dimethylaminoethyl)-1H-indol-5-yl]naphthalene-1-sulphonamide.

[9] N-[3-(2-dimethylamino-ethyl)-1H-indol-5-yl]-6-chloroimidazo[2,1-b]thiazol-5-sulphonamide.

[10] N-[3-(1-methylpiperidin-4-yl)-1H-indol-5-yl]-5-chloro-3-methylbenzo[b]thiophene-2-sulphonamide.

[11] N-[3-(1-methylpiperidin-4-yl)-1H-indol-5-yl]-5-chloro-3-methylbenzo[b]thiophene 2-sulphonamide hydrochloride.

[12] N-[3-(1-methylpiperidin-4-yl)-1H-indol-5-yl]naphthalene-1-sulphonamide.

[13] N-[3-(1-methylpiperidin-4-yl)-1H-indol-5-yl]naphthalene-1-sulphonamide hydrochloride.

[14] N-[3-(1-methylpiperidin-4-yl)-1H-indol-5-yl]-5-chlorothiophene-2-sulphonamide.

[15] N-[3-(1-methylpiperidin-4-yl)-1H-indol-5-yl]-4-phenylbenzenesulphonamide.

[16] N-[3-(1-methylpiperidin-4-yl)-1H-indol-5-yl]quinoline-8-sulphonamide.

[17] N-[3-(2-diethylaminoethyl)-1H-indol-5-yl]naphthalene-2-sulphonamide.

[18] N-[3-(1-methyl-1,2,3,6-tetrahydropyridin-4-yl)-1H-indol-5-yl]naphthalene-1-sulphonamide.

[19] N-[3-(4-methylpiperazin-1-yl)methyl-1H-indol-5-yl]-5-chloro-3-methylbenzo[b]thiophene-2-sulphonamide.

[20] N-[3-(2-dimethylaminoethyl)-1H-indol-5-yl]-5-(2-pyridil)thiophene-2-sulphonamide.

[21] N-[3-(2-dimethylaminoethyl)-1H-indol-5-yl]-2,1,3-benzothiadiazol-4-sulphonamide.

[22] N-[3-(2-dimethylaminoethyl)-1H-indol-5-yl]quinoline-8-sulphonamide.

[23] N-[3-(2-dimethylaminoethyl)-1H-indol-5-yl]-5-chloronaphthalene-2-sulphonamide.

[24] N-[3-(2-dimethylaminoethyl)-1H-indol-5-yl]-4-phenoxybenzenesulphonamide.

[25] N-[3-(2-dimethylaminoethyl)-1H-indol-5-yl]-4-phenylbenzenesulphonamide.

[26] N-[3-(2-diethylaminoethyl)-1H-indol-5-yl]-N-ethylnaphthalene-2-sulphonamide.

[27] N-{3-[2-(morpholin-4-yl)ethyl]-1H-indol-5-yl}-5-chloro-3-methylbenzo[b]thiophene-2-sulphonamide.

[28] N-{3-[2-(morpholin-4-yl)ethyl]-1H-indol-5-yl}naphthalene-1-sulphonamide.

[29] N-[3-(2-diethylaminoethyl)-1H-indol-5-yl]naphthalene-2-sulphonamide.

[30] N-[3-dimethylaminomethyl-1H-indol-5-yl]-5-chloro-3-methylbenzo[b]thiophene-2-sulphonamide.

[31] N-[3-(2-dipropylaminoethyl)-1H-indol-5-yl]naphthalene-1-sulphonamide.
[32] N-[3-(2-dipropylaminoethyl)-1H-indol-5-yl]-5-chloro-3-methylbenzo[b]thiophene-2-sulphonamide.
[33] N-[3-(2-dibutylaminoethyl)-1H-indol-5-yl]-5-chloro-3-methylbenzo[b]thiophene-2-sulphonamide.
[34] N-[3-(2-dibutylaminoethyl)-1H-indol-5-yl]naphthalene-1-sulphonamide.
[35] N-[3-(2-diethylaminoethyl)-1H-indol-5-yl]-5-chloronaphthalene-1-sulphonamide.
[36] N-[3-(2-diethylaminoethyl)-1H-indol-5-yl]-trans-β-styrenesulphonamide.
[37] N-[3-(4-methylpiperazin-1-yl)methyl-1H-indol-5-yl]-trans-β-styrenesulphonamide.
[38] N-[3-(octahydroindolizin-7-yl)-1H-indol-5-yl]-5-chloro-3-methylbenzo[b]thiophene-2-sulphonamide.
[39] N-[3-(2-diethylaminoethyl)-1H-indol-5-yl]-6-chloroimidazo[2,1-b]thiazol-5-sulphonamide.
[40] N-{3-[2-(morpholin-4-yl)ethyl]-1H-indol-5-yl}naphthalene-2-sulphonamide.
[41] N-[3-(4-methylpiperazin-1-yl)methyl-1H-indol-5-yl]-α-toluenesulphonamide.
[42] N-[3-(3-diethylaminopropyl)-1H-indol-5-yl]naphthalene-2-sulphonamide.
[43] N-[3-(3-diethylaminopropyl)-1H-indol-5-yl]-5-chloro-3-methylbenzo[b]thiophene-2-sulphonamide.
[44] N-{3-[2-(pyrrolidin-1-yl)ethyl]-1H-indol-5-yl}-5-chloro-3-methylbenzo[b]thiophene-2-sulphonamide.
[45] N-{3-[2-(pyrrolidin-1-yl)ethyl]-1H-indol-5-yl}naphthalene-1-sulphonamide.
[46] N-{3-[2-(pyrrolidin-1-yl)ethyl]-1H-indol-5-yl}naphthalene-2-sulphonamide.
[47] N-[3-(2-dipropylaminoethyl)-1H-indol-5-yl]naphthalene-2-sulphonamide.
[48] N-[3-(2-dimethylaminoethyl)-1H-indol-5-yl]-5-chloronaphthalene-1-sulphonamide.
[49] N-[3-(2-dimethylaminoethyl)-1H-indol-5-yl]naphthalene-2-sulphonamide.
[50] N-{3-[2-(morpholin-4-yl)ethyl]-1H-indol-5-yl}quinoline-8-sulphonamide.
[51] N-{3-[2-(morpholin-4-yl)ethyl]-1H-indol-5-yl}4-phenylbenzenesulphonamide.
[52] N-[3-(4-methylpiperazin-1-yl)ethyl-1H-indol-5-yl]naphthalene-2-sulphonamide.
[53] N-[3-(4-methylpiperazin-1-yl)ethyl-1H-indol-5-yl]-5-chloronaphthalene-1-sulphonamide.

The present invention also relates to the physiologically acceptable salts of the compounds with the general formula (I), particularly the addition salts of mineral acids such as hydrochloric, hydrobromic, phosphoric, sulphuric, nitric acids, and of organic acids such as citric, maleic, fumaric, tartaric acids or their derivatives, p-toluensulphonic acid, methansulphonic acid, camphorsulphonic acid, etc.

The new derivatives with the general formula (I), wherein $R_1$, $R_2$, $R_3$, $R_4$, n and A are as indicated above, can be prepared according to the following methods:

Method A

By reacting a compound with the general formula (II) or one of its suitably protected derivatives

(II)

wherein A is as indicated previously in the general formula (I) and X is an acceptable salient group including a halogen atom, particularly chlorine:

with a 5-aminoindol with the general formula (III), or one of its suitably protected derivatives;

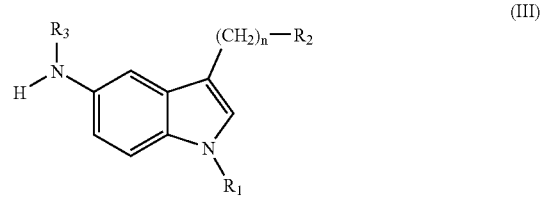

(III)

wherein n, $R_1$, $R_2$ and $R_3$ are as indicated previously in the general formula (I);

in order to obtain the corresponding sulphonamide and, optionally, eliminating from it the protective groups and/or forming a pharmacologically acceptable salt.

The reaction between the compounds with the general formula (II) and (III) is carried out in the presence of an organic solvent such as an alkyl ether, particularly diethyl ether, or a cycloalkyl, particularly tetrahydrofurane or dioxane, a halogenated organic hydrocarbon, particularly methylene chloride or chloroform, an alcohol, particularly methanol or ethanol, an aprotic dipolar solvent, particularly acetonitryl, pyridine or dimethylformamide, or any other suitable solvent.

The reaction preferably is carried out in the presence of a suitable inorganic base such as hydroxides and carbonates of alkali metals, or in the presence of an organic base, particularly triethylamine or pyridine.

The most suitable reaction temperatures range from 0° C. to ambient temperature, and the reaction time is between 5 minutes and 24 hours.

The resulting sulphonamide can be isolated by evaporating the solvent, adding water and eventually adjusting the pH so that it is obtained as a solid that can be isolated by filtration; or it can be extracted by a solvent immiscible in water such as chloroform and purified by chromatography or recrystallisation from a suitable solvent.

The compounds with the general formula (II) are commercially available or can be prepared according to standard methods or by methods analogous to those described in the literature [E. E. Gilbert, *Synthesis,* 1969, 1, 3] and the compounds with the general formula (III) can be prepared according to standard methods or by methods analogous to those described in the literature [J. E. Macor, R. Post and K. Ryan, *Synt Comm.,* 1993, 23,1,65-72.; J. Guillaume, C. Dumont, J. Laurent and N. Nédélec, *Eur. J. Med. Chem.,* 1987, 22, 3343; M. L. Saccarello, R. Stradi, *Synthesis,* 1979, 727].

Method B

The compounds with the general formula (I), wherein $R_1$, $R_2$, $R_4$, n and A are as indicated above and $R_3$ represents a $C_1$-$C_4$ alkyl, can be prepared by alkylation of a compound with the general formula (I), wherein $R_1$, $R_2$, $R_4$, n and A are as indicated above and $R_3$ represents an atom of hydrogen, with an alkyl halogenide or a dialkyl sulphate.

The reaction preferably is carried out in the presence of a suitable base such as hydroxides and carbonates of alkali metals, metal hydrides, alkoxides such as sodium methoxide or potassium terbutoxide, organometallic compounds such as butyl lithium or terbutyl lithium, in the presence of an organic solvent such as an alkyl ether, particularly diethyl ether, or cycloalkyl, particularly tetrahydrofurane or dioxane, a hydrocarbon, particularly toluene, an alcohol, particularly methanol or ethanol, an aprotic dipolar solvent, particularly acetonitryl, pyridine or dimethylformamide, or any other suitable solvent. The most suitable temperatures are between 0° C. and the boiling point of the solvent, and reaction times are between 1 and 24 hours.

The resulting sulphonamide can be isolated by concentrating the filtrate at reduced pressure, adding water and eventually adjusting the pH so that it is obtained as a solid that can be isolated by filtration, or it can be extracted with a solvent immiscible in water such as chloroform and purified by chromatography or recrystallisation from a suitable solvent.

Method C

By condensation of a compound with the general formula (I) wherein $R_1$, $R_3$, and A are as indicated above, n=0 and $R_2$ represents an atom of hydrogen, with a suitably substituted 4-piperidone the corresponding compound is obtained with the general formula (I) wherein $R_1$, $R_3$, and A are as indicated above, n=0 and $R_2$ represents a suitably substituted 1,2,3,6-tetrahydropyridine-4-yl radical.

The reaction can take place in both an acid and a basic medium, in a suitable solvent at temperatures between 25 and 150° C.

suitable basic conditions include inorganic bases such as sodium or potassium hydroxide, or organic bases such as pyrrolidine or triethylamine in solvents such as methanol or ethanol. Preferably, solutions of sodium methoxide in methanol at reflux. Reaction times range from 1 to 48 hours.

suitable acidic conditions include hydrochloric acid in ethanol or trifluoroacetic acid in acetic acid at temperatures between 50 and 100° C. and reaction times ranging from 1 to 48 hours.

The resulting sulphonamide can be isolated by dilution in water, eventually adjusting the pH, to obtain a solid that can be isolated by filtration; or it can be extracted with a solvent immiscible in water such as chloroform and purified by chromatography or by recrystallisation from a suitable solvent.

The compounds with the general formula (I) wherein $R_1$, $R_3$, and A are as indicated above, n=0 and $R_2$ represents an atom of hydrogen, can be prepared according to the method A from a 5-aminoindol.

Method D

The compounds with the general formula (I) wherein $R_1$, $R_3$, and A are as indicated above, n=0 and $R_2$ represents a suitably substituted 4-piperidinyl radical, can be prepared by reducing a compound with the general formula (I) wherein $R_1$, $R_3$, and A are as indicated above, n=0 and $R_2$ represents a suitably substituted 1,2,3,6-tetrahydropyridin-4-yl radical prepared according to the method C.

Hydrogenation takes place with the aid of a metallic catalyst such as palladium, platinum or rhodium on a support such as carbon, aluminum oxide or barium sulphate, preferably palladium over carbon, with an initial hydrogen pressure of between 1 and 10 atmospheres, preferably between 2 and 5 atmospheres, in a solvent such as methanol or ethanol. The reaction time ranges from 1 hour to 3 days.

The resulting sulphonamide can be isolated by filtering the catalyst and concentrating the filtrate at reduced pressure. The product recovered can be used as is or it can be purified by chromatography or by recrystallisation from a suitable solvent.

Method E

The pharmacologically acceptable salts of compounds with the general formula (I) can be conventionally prepared by reaction with a mineral acid, such as hydrochloric, hydrobromic, phosphoric, sulphuric, nitric acids or with organic acids such as citric, maleic, fumaric, tartaric acids or their derivatives, p-toluensulphonic acid, methansulphonic acid, etc., in a suitable solvent such as methanol, ethanol, ethyl ether, ethyl acetate, acetonitryl or acetone and obtained with the usual techniques of precipitation or crystallisation of the corresponding salts.

During one of the synthesis sequences described, or in the preparation of the sintones used it may be necessary and/or desirable to protect sensitive or reactive groups in some of the molecules employed. This can be performed by means of conventional protective groups such as those described in the literature (Protective groups in Organic Chemistry, ed J. F. W. McOmie, Plenum Press, 1973; T. W. Greene & P. G. M. Wuts, Protective Groups in Organic Chemistry, John Wiley & sons, 1991]. The protective groups can be eliminated in a suitable latter stage by known methods.

The invention provides pharmaceutical compositions that comprise, in addition to an acceptable pharmaceutical excipient, at least one compound with the general formula (I) or one of its physiologically acceptable salts. The invention also relates to the use of a compound with the general formula (I) and its physiologically acceptable salts in the preparation of a medicament having $5-HT_6$ serotonin receptor antagonistic activity, useful for preventing or treating various disorders of the Central Nervous System, and particularly anxiety, depression, cognitive memory disorders and senile dementia processes, and other dementias in which predominates a cognition deficit, psychosis, infant hyperkinesia (ADHD, attention deficit/hyperactivity disorder) and other disorders mediated by the $5-HT_6$ serotonin receptor in mammals, including man.

The following examples show the preparation of novel compounds according to the invention. Also described in the affinity for the receptor $5HT_6$ of serotonin, as well as galenic formulae applicable to the compounds object of the invention. The examples provided below are provided for purposes of illustration only and are in no way meant as a definition of the limits of the invention.

Method A

EXAMPLE 7

Preparation of N-[3-(2-dimethylaminoethyl)-1H-indol-5-yl]-5-chloro-3-methyl-benzo[b]thiophene-2-sulphonamide To a solution of 3.05 g (15 mMol) of 5-amino-3-(2-dimethylaminoethyl)-1H-indol in 100 ml of pyridine is added dropwise at ambient temperature a solution of 4.21 g (15 mMol) of 5-chloro-3-methyl-benzo[b]thiophene-2-sulphonyl chloride in 20 ml of pyridine. The reaction mixture is stirred at ambient temperature for 20 hours. It is then evaporated to dryness, slightly alkalinised with diluted ammonia and dissolved in ethyl acetate. The organic phase is washed with water and a saturated solution of sodium bicarbonate, it is separated and dried with anhydrous sodium sulphate. The organic solution is evaporated to dryness and the resulting solid is repeatedly washed with ethyl ether, to yield 5.5 g (82%) of N-[3-(2-dimethylaminoethyl)-1H-indol-5-yl]-5-chloro-3-methyl-benzo[b]thiophene-2-sulphonamide as a solid with m.p.=226-227° C.

Method B

EXAMPLE 26

Preparation of N-[3-(2-diethylaminoethyl)-H-indol-5-yl]-N-ethyl-naphthalene-2-sulphonamide To a mixture of 285 mg (0.7 mMol) of N-[3-(2-diethylaminoethyl)-1H-indol-5-yl]naphthalene-2-sulphonamide (example 17) and 80 mg (0.7 mMol) of potassium t-butoxide in 3 ml of DMSO are stirred for 30 minutes at ambient temperature. Then are added 105 mg (0.7 mMol) of ethyl iodide and left with stirring for 3 hours. Water is added and is extracted with ethyl acetate. The organic solution is evaporated to dryness and the resulting crude is purified by chromatography on silica gel, using as an eluent mixtures of methylene chloride/methanol/ammonia, yielding N-[3-(2-diethylaminoethyl)-

1H-indol-5-yl]-N-ethyl-naphthalene-2-sulphonamide as a solid with m.p.=49-50° C.

Method C

EXAMPLE 18

Preparation of N-[3-(1-methyl-1,2,3,6-tetrahydropyridin-4-yl)-1H-indol-5-yl]naphthalene-1-sulphonamide To a solution of 712 mg (13.2 mMol) of sodium methoxide in 100 ml of methanol are added 850 mg (2.64 mMol) of N-[1H-indol-5-yl]naphthalene-1-sulphonamide followed by 596 mg (5.28 mMol) of 1-methyl-4-piperidone and the resulting solution is heated to reflux for 48 hours. The reaction mixture is concentrated at reduced pressure and the residue obtained is purified by chromatography over silica gel, using as eluent mixtures of methylene chloride/methanol/ammonia, to yield 573 mg (52%) of N-[3-(1-methyl-1,2,3,6-tetrahydropyridin-4-yl)-1H-indol-5-yl]naphthalene-1-sulphonamide as a solid with m.p.=244-245° C.

Method D

EXAMPLE 12

Preparation of N-[3-(1-methyl-piperidin-4-yl)-1H-indol-5-yl]naphthalene-1-sulphonamide To a solution of 417 mg (1 mMol) of N-[3-(1-methyl-1,2,3,6-tetrahydropyridin-4-yl)-1H-indol-5-yl]naphthalene-1-sulphonamide in 50 ml of methanol are added 100 mg of 5% palladium on carbon. The mixture is hydrogenated at ambient temperature at an initial hydrogen pressure of 3 atmospheres for 20 hours. The reaction mixture is filtered and the filtrate is concentrated at reduced pressure to provide a crude that is suspended in ethyl ether, yielding 272 mg (65%) of N-[3-(1-methyl-piperidin-4-yl)-1H-indol-5-yl]naphthalene-1-sulphonamide as a solid with m.p.=254-256° C.

Method E

EXAMPLE 3

Preparation of N-[3-(2-diethylaminoethyl)-1H-indol-5-yl]naphthalene-1-sulphonamide hydrochloride 1.05 g (2.5 mMol) of N-[3-(2-diethylaminoethyl)-1H-indol-5-yl]naphthalene-1-sulphonamide (example 2) are dissolved in 10 ml of ethanol and 0.6 ml are added of a 4.2 N solution of hydrochloric acid in ethanol. It is allowed to crystallise at ambient temperature. N-[3-(2-diethylaminoethyl)-1H-indol-5-yl]naphthalene-1-sulphonamide hydrochloride is obtained as a solid with m.p.=255-257° C.

The melting point and spectroscopic data for identifying some of the compounds object of the present invention are shown in the following table:

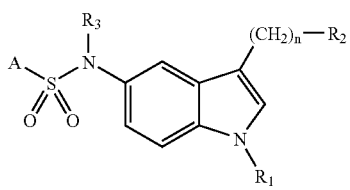

| Ex | $R_1$ | $R_2$ | n | $R_3$ | A | Salt | m.p. ° C. | IR cm$^{-1}$ | $^1$H-RMN (300 MHz), δ (solvent) |
|---|---|---|---|---|---|---|---|---|---|
| 1 | H | (CH$_3$CH$_2$)$_2$N— | 2 | H | 5-chloro-3-methyl-2-benzothiophenyl | — | 170–173 | 3387, 2970, 2931, 1466, 1236, 1158, 1107, 1080, 993, 862, 805, 657, 565. | 0.88(t, 6H, J=7.1 Hz); 2.28(s, 3H); 2.30–2.46(m, 6H); 2.58(m, 2H); 6.85(dd, 1H, J=8.6, 2.0 Hz); 7.10(m, 2H); 7.20(d, 1H, J=8.6 Hz); 7.50(dd, 1H, J=8.7, 2.0 Hz); 7.90(d, 1H, J=2.0 Hz); 7.98(d, 1H, J=8.7 Hz); 10.10(bb, 1H); 10.80(s, 1H) (DMSO-d6) |
| 2 | H | (CH$_3$CH$_2$)$_2$N— | 2 | H | 1-methylnaphthyl | — | 170 | 3451, 3337, 2972, 1466, 1319, 1237, 1157, 1132, 1091, 991, 770, 675, 583, 481. | 0.90(t, 6H, J=7.1 Hz); 2.33–2.55(m, 8H); 6.69(dd, 1H, J=8.7, 1.8 Hz); 6.95(s, 1H); 7.02(d, 1H, J=1.8 Hz); 7.05(d, 1H, J=8.7 Hz); 7.47(t, 1H, J=7.7 Hz); 7.63(m, 1H); 7.70(m, 1H); 8.01(m, 2H); 8.12(d, 1H, J=7.5 Hz); 8.77(d, 1H, J=8.1 Hz); 10.10(bb, 1H); 10.66(s, 1H) (DMSO-d6) |
| 3 | H | (CH$_3$CH$_2$)$_2$N— | 2 | H | 1-methylnaphthyl | HCl | 255-257 | 3378, 3065, 2558, 2489, 1460, 1317, 1162, 1143, 1131, 811, 687, 602, 588. | 1.22(t, 6H, J=7.2 Hz); 2.91–3.18(m, 8H); 6.65(d, 1H, J=8.6 Hz); 7.08(d, 1H, J=8.6 Hz); 7.17(s, 1H); 7.20(d, 1H, J=1.8 Hz); 7.54(t, 1H, J=7.8 Hz); 7.63(m, 1H); 7.70(m, 1H); 8.03(d, 1H, J=7.8 Hz); 8.08(d, 1H, J=7.1 Hz); 8.14(d, 1H, J=8.2 Hz); 8.79(d, 1H, J=8.4 Hz); 10.26(s, 1H); 10.90(bb, 1H); 11.01(s, 1H) (DMSO-d6) |

-continued

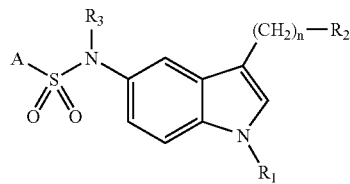

| Ex | R₁ | R₂ | n | R₃ | A | Salt | m.p. °C. | IR cm⁻¹ | ¹H-RMN (300 MHz), δ (solvent) |
|---|---|---|---|---|---|---|---|---|---|
| 4 | H | (CH₃CH₂)₂N— | 2 | H | 2,5-dichlorophenyl (with methyl) | — | 168-170 | 3309, 3047, 2974, 1566, 1467, 1235, 1167, 1143, 1116, 1001, 910, 799, 672, 587. | 0.95(t, 6H, J=7.1 Hz); 2.44-2.58(m, 6H); 2.66(m, 2H); 6.79(dd, 1H, J=8.6, 1.7 Hz); 7.08(d, 1H, J=0.9 Hz); 7.13(d, 1H, J=1.7 Hz); 7.23(d, 1H, J=8.6 Hz); 7.58(m, 2H); 7.87(m, 1H); 9.95(bb, 1H); 10.82(s, 1H). (DMSO-d6) |
| 5 | H | (CH₃CH₂)₂N— | 2 | H | 4-methylbiphenyl | — | 161-163 | 3387, 2971, 1323, 1157, 1095, 765, 670, 590 | 0.89(t, 6H, J=7.1 Hz); 2.32-2.55(m, 6H); 2.62(m, 2H); 6.85(d, 1H, J=8.6 Hz); 7.08(d, 1H, J=2.0 Hz); 7.13(s, 1H); 7.18(d, 1H, J=8.6 Hz); 7.33-750 (m, 3H); 7.64(d, 2H, J=7.5 Hz); 7.72(sys AB, 2H, J=8.6 Hz); 7.78(sys AB, 2H, J=8.6 Hz); 9.80(bb, 1H); 10.75(s, 1H). (DMSO-d6) |
| 6 | H | (CH₃CH₂)₂N— | 2 | H | 5-chloro-2-methylthiophene | — | 180-181 | 3375, 2978, 1467, 1417, 1236, 1212, 1115, 994, 624. | 0.96(t, 6H, J=7.1 Hz); 2.52(m, 4H); 2.57(m, 2H); 2.66(m, 2H); 6.83(dd, 1H, J=8.6, 1.9 Hz); 7.11(d, 1H, J=4.0 Hz); 7.14(d, 1H, J=1.9 Hz); 7.17(d, 1H, J=1.9 Hz); 7.20-7.24(m, 2H); 10.01(bb. 1H); 10.81(s, 1H). (DMSO-d6) |
| 7 | H | (CH₃)₂N— | 2 | H | 5-chloro-2,3-dimethylbenzothiophene | — | 226-227 | 3422, 3238, 1332, 1155, 1114, 1079, 986, 861, 803, 655, 564. | 2.04(s, 6H); 2.23(m, 2H); 2.28(s, 3H); 2.59(m, 2H); 6.83(dd, 1H, J=8.4, 1.5 Hz); 7.09(s, 2H); 7.19(d, 1H, J=8.4 Hz); 7.49(dd, 1H, J=8.7, 1.6 Hz); 7.91(d, 1H, J=1.6 Hz); 7.99(d, 1H, J=8.7 Hz); 10.13(bb, 1H), 10.79(s, 1H) (DMSO-d6) |
| 8 | H | (CH₃)₂N— | 2 | H | 1-methylnaphthalene | — | 203-205 | 3357, 1475, 1282, 1157, 1127, 990, 957, 809, 773, 613, 587, 557, 498. | 2.09(s, 6H); 2.21(m, 2H); 2.54(m, 2H); 6.69(dd, 1H, J=8.6, 1.7 Hz); 6.94 (s, 1H); 7.03(s, 1H); 7.06(d, 1H, J=8.1 Hz); 7.49(t, 1H, J=7.8 Hz); 7.64(m, 1H); 7.71(m, 1H); 8.02(m, 2H); 8.13(d, 1H, J=8.1 Hz); 8.79(d, 1H, J=8.4 Hz); 10.10(bb, 1H); 10.68(s, 1H) (DMSO-d6) |
| 9 | H | (CH₃)₂N— | 2 | H | 6-chloro-5-methylimidazo[2,1-b]thiazole | — | 215 (desc) | 3247, 3094, 1467, 1272, 1261, 1230, 625 | 2.17(s, 6H); 2.36(m, 2H); 2.65(m, 2H); 6.77(dd, J=8.6, 1.7 Hz, 1H); 7.07(s, 1H); 7.09(s, 1H); 7.18(d, J=8.6 Hz, 1H); 7.51(d, J=4.5 Hz, 1H); 7.81(d, J=4.5 Hz, 1H); 10.80(s, 1H) (DMSO-d6) |
| 10 | H | 1-methyl-4-piperidinyl (H₃C—N-piperidine) | 0 | H | 5-chloro-2,3-dimethylbenzothiophene | — | 250 (desc) | 3407, 2390, 1466, 1334, 1156, 113, 1080, 651, 565 | 1.53-1.80(m, 4H); 2.26(s, 3H); 2.39-2.71(m, 6H); 3.02(d, 2H, J=8.8 Hz); 6.76(d, 1H, J=8.8 Hz); 7.05(s, 1H); 7.11(s, 1H); 7.19(d, 1H, J=8.8 Hz); 7.51(d, 1H, J=8.7 Hz); 7.91(s, 1H); 8.00(d, 1H, J=8.7 Hz); 10.10(bb, 1H); 10.90(s, 1H) (DMSO-d6) |

-continued

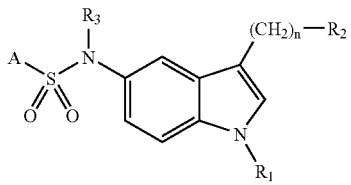

| Ex | R₁ | R₂ | n | R₃ | A | Salt | m.p. °C. | IR cm⁻¹ | ¹H-RMN (300 MHz), δ (solvent) |
|---|---|---|---|---|---|---|---|---|---|
| 11 | H | H₃C—N(piperidine)— | 0 | H | 5-chloro-2,3-dimethylbenzothiophene | HCl | 220 (desc) | 3423, 3214, 3043, 2942, 2688, 1464, 1317, 1149, 1114, 1080, 748, 670, 646 | 1.75-1.92(m, 4H); 2.31(s, 3H); 2.66(s, 3H); 2.80(m, 1H); 2.95(m, 2H); 3.24(d, 2H, J=11.4 Hz); 6.76(d, 1H, J=8.7 Hz); 7.07(s, 1H); 7.19(m, 2H); 7.50(d, 1H, J=8.6 Hz); 7.93(s, 1H); 8.01(d, 1H, J=8.6 Hz); 8.34(s, 1H); 10.90(bb, 1H); 11.01(s, 1H). (DMSO-d6) |
| 12 | H | H₃C—N(piperidine)— | 0 | H | 1-methylnaphthalene | — | 254-256 | 3343, 2938, 2929, 1470 1154, 1121, 1108, 988, 947, 805, 769, 589. | 1.49(m, 2H); 1.61(m, 2H); 2.14(m, 2H); 2.30(s, 3H); 2.40(m, 1H); 2.90(d, 2H, J=10.6 Hz); 6.65(d, 1H, J=8.6 Hz); 6.90(s, 1H); 6.96(s, 1H); 7.05(d, 1H, J=8.6 Hz); 7.46(dt, 1H, J=7.51, 1.83 Hz); 7.64(m, 1H); 7.71(m, 1H); 7.99(d, 1H, J=8.6 Hz); 8.03(d, 1H, J=8.6 Hz); 8.12(d, 1H, J=8.2 Hz); 8.77(d, 1H, J=8.6 Hz); 10.07(bb, 1H); 10.71(s, 1H) (DMSO-d6) |
| 13 | H | H₃C—N(piperidine)— | 0 | H | 1-methylnaphthalene | HCl | 212 (desc) | 3423, 3269, 3114, 2955, 2733, 1469, 1321, 1155, 1133, 947, 769. | 1.80(m, 4H); 2.74(m, 4H); 3.04(m, 2H); 3.39(m, 2H); 6.63(d, 1H, J=8.6 Hz); 7.00(s, 1H); 7.08(d, 1H, J=8.6 Hz); 7.49(t, 1H, J=7.7 Hz); 7.60-7.77(m, 2H); 8.04(d, 2H, J=7.5 Hz); 8.13(d, 1H, J=8.2 Hz); 8.79(d, 1H, J=8.2 Hz); 10.16(s, 1H); 10.66(bb, 1H); 10.88(s, 1H). (DMSO-d6) |
| 14 | H | H₃C—N(piperidine)— | 0 | H | 5-chloro-2-methylthiophene | — | 284 (desc) | 3371, 2943, 1468, 1410, 1324, 1148, 993, 604. | 1.62(m, 2H); 1.78(d, 2H, J=11.7 Hz); 1.99(m, 2H); 2.18(s, 3H); 2.55(m, 1H); 2.84(d, 2H, J=10.6 Hz); 6.81(d, 1H, J=8.6 Hz); 7.07(s, 1H); 7.13(m 1H); 7.16(s, 1H); 7.20-7.26(m, 1H); 9.90(bb, 1H); 10.83(s, 1H). (DMSO-d6) |
| 15 | H | H₃C—N(piperidine)— | 0 | H | 4-methylbiphenyl | — | 247-248 | 3361, 2936, 1318, 1155, 1095, 767, 670, 587. | 1.52(s, 2H); 1.67(m, 2H); 1.85(m, 2H) 2.08(s, 3H); 2.44(m, 1H); 2.67(d, 2H, J=10.25 Hz); 6.83(d, 1H, J=8.4 Hz); 7.01(s, 1H); 7.03(s, 1H); 7.19(d, 1H, J=8.4 Hz); 7.35-7.50(m, 3H); 7.63-7.73(m, 4H); 7.79(sys AB, 2H, J=7.6 Hz); 9.71(bb, 1H); 10.76(s, 1H) (DMSO-d6). |
| 16 | H | H₃C—N(piperidine)— | 0 | H | 8-methylquinoline | — | 280 (desc) | 3398, 3257, 2933, 1161, 1143, 789, 589. | 1.25-1.52(m, 4H); 1.85(m, 2H); 2.18(s, 3H); 2.27(m, 1H); 2.74(d, J=11.4 Hz, 2H); 6.72(dd, J=8.6, 2.0 Hz, 1H); 6.83(d, J=1.5 Hz, 1H); 6.90(d, J=2.0 Hz, 1H); 7.02(d, J=8.6 Hz, 1H); 7.57(m, 1H); 7.74(dd, J=8.4, 4.3 Hz, 1H); 8.12(dd, J=7.3, 1.3 Hz, 1H); 8.19(dd, J=8.2, 1.3 Hz, 1H); 8.52(dd, J=8.4, 1.7 Hz, 1H); 9.21(dd, J=4.3, 1.7 Hz, 1H); 9.36(s, 1H); 10.64(s, 1H). (DMSO-d6). |

-continued

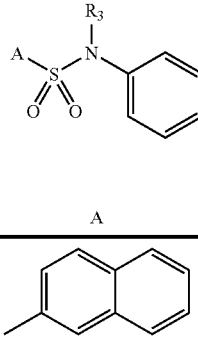

| Ex | R₁ | R₂ | n | R₃ | A | Salt | m.p. °C. | IR cm⁻¹ | ¹H-RMN (300 MHz), δ (solvent) |
|---|---|---|---|---|---|---|---|---|---|
| 17 | H | (CH₃CH₂)₂N— | 2 | H | 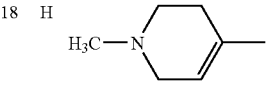 | — | 172-173 | 3199, 2970, 2930, 2870, 1327, 1153, 1130, 1110, 1075, 956, 676, 658, 551, 476. | 0.87(t, J=7.1 Hz, 6H); 2.39(m, 6H); 2.55(m, 2H); ); 6.82(d, J=8.6 Hz, 1H); 7.05(s, 1H); 7.09(s, 1H); 7.13(d, J=8.6 Hz, 1H); 7.60(m, 2H); 7.73(d, J=8.6 Hz, 1H); 7.95(d, J=7.9 Hz, 1H); 8.01(m, 2H); 8.26(s, 1H); 9.86(bb, 1H); 10.71(s, 1H). (DMSO-d6). |
| 18 | H | 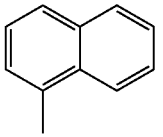 | 0 | H | 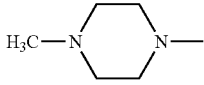 | — | 244-245 (desc) | 3346, 2943, 1474, 1283, 1261, 1156, 1123, 801, 771, 589, 503. | 2.25(s, 3H); 2.31(m, 2H); 2.46(m, 2H); 2.90(m, 2H); 5.34(s, 1H); 6.78(dd, J=8.6, 2.0 Hz, 1H); 7.09(d, J=1.5 Hz, 1H); 7.14(d, J=8.6 Hz, 1H); 7.25(d, J=2.0 Hz, 1H); 7.49(t, J=7.8 Hz, 1H); 7.66(m, 1H); 7.75(m, 1H); 8.04(m, 2H); 8.14(d, J=8.2 Hz, 1H); 8.83(d, J=8.6 Hz, 1H); 10.14(bb, 1H); 11.03(s, 1H). (DMSO-d6). |
| 19 | H | 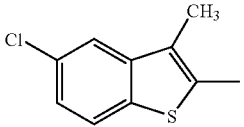 | 1 | H | 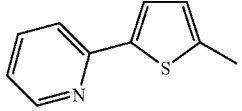 | — | 230 (desc) | 2796, 1452, 1316, 1149, 1114, 1080, 1001, 810, 646, 559. | 1.80-2.26(m, 8H); 2.04(s, 3H); 2.30(s, 3H); 3.41(s, 2H); 6.89(dd, J=8.6, 1.56 Hz, 1H); 7.16(s, 1H); 7.22(d, J=8.6 Hz 1H); 7.29(s, 1H); 7.49(dd, J=8.7, 1.7 Hz, 1H); 7.90(d, J=1.7 Hz, 1H); 7.98(d, J=8.7 Hz, 1H); 10.13(bb, 1H); 10.93(s, 1H). (DMSO-d6). |
| 20 | H | (CH₃)₂N— | 2 | H | 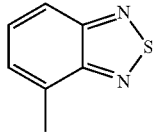 | — | 209-211 | 3377, 2951, 2798, 1469, 1429, 1321, 1158, 777, 594. | 2.05(s, 6H); 2.32(m, 2H); 2.65(m, 2H); 6.86(dd, J=8.6, 1.8 Hz, 1H); 7.10(d, J=1.8 Hz, 1H); 7.18(d, J=1.8 Hz, 1H); 7.21(d, J=8.6 Hz, 1H); 7.32(dd, J=7.5, 4.6 Hz, 1H); 7.36(d, J=3.9 Hz, 1H); 7.71(d, J=3.9 Hz, 1H); 7.83(m, 1H); 7.93(m, 1H); 8.49(d, J=4.6 Hz, 1H); 9.97(bb, 1H); 10.79(s, 1H). (DMSO-d6). |
| 21 | H | (CH₃)₂N— | 2 | H | 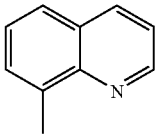 | — | 192 | 3321, 2949, 1474, 1327, 1152, 1138, 1104, 981, 614. | 2.10(s, 6H); 2.21(m, 2H); 2.56(m, 2H); 6.72(d, J=8.6 Hz, 1H); 6.96(s, 1H); 7.03(s, 1H); 7.07(d, J=8.6 Hz, 1H); 7.70(m, 1H); 8.07(d, J=7.0 Hz, 1H); 8.29(d, J=8.8 Hz, 1H); 10.14(bb, 1H); 10.69(s, 1H). (DMSO-d6). |
| 22 | H | (CH₃)₂N— | 2 | H | 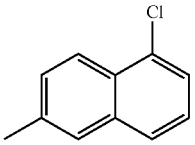 | — | 250 (desc) | 3252, 2857, 1459, 1426, 1333, 1161, 1144, 789, 680, 589. | 2.07(s, 6H); 2.16(m, 2H); 2.51(m, 2H); 6.73(dd, J=8.6, 1.8 Hz, 1H); 6.94(s, 1H) 6.99(s, 1H); 7.02(d, J=8.6 Hz, 1H); 7.59(t, J=7.8 Hz, 1H); 7.73(dd, J=8.4, 4.1 Hz, 1H); 8.18(m, 2H); 8.50(dd, J=8.4, 1.5 Hz, 1H); 9.20(dd, J=4.1, 1.5 Hz, 1H); 9.45(bb, 1H); 10.64(s, 1H). (DMSO-d6). |
| 23 | H | (CH₃)₂N— | 2 | H |  | — | 230-240 (desc) | 3404, 2944, 2918, 2855, 1465, 1332, 1157, 1140, 1080, 650, 639, 526. | 2.01(s, 6H); 2.18(m, 2H); 2.57(m, 2H); 6.81(dd, J=8.6, 1.7 Hz, 1H); 7.02 (s, 1H); 7.05(d, J=1.7 Hz, 1H); 7.15(d, J=8.6 Hz, 1H); 7.57(m, 1H); 7.82(d, J=7.5 Hz, 1H); 7.91(d, J=8.9 Hz, 1H); 8.06(d, J=8.2 Hz, 1H); 8.29(d, J=8.9 Hz, 1H); 8.35(s, 1H); 9.94(bb, 1H); 10.74(s, 1H). (DMSO-d6). |

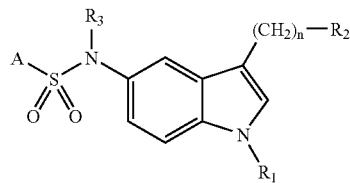

| Ex | R₁ | R₂ | n | R₃ | A | Salt | m.p. °C. | IR cm⁻¹ | $^1$H-RMN (300 MHz), δ (solvent) |
|---|---|---|---|---|---|---|---|---|---|
| 24 | H | (CH₃)₂N— | 2 | H | 4-phenoxyphenyl | — | 152-154 | 3232, 2862, 2827, 2785, 1583, 1488, 1333, 1248, 1155, 1091, 755, 693, 571, 541. | 2.16(s, 6H); 2.37(m, 2H); 2.66(m, 2H); 6.80(d, J=8.6 Hz, 1H); 6.96-7.12(m, 6H); 7.14-7.25(m, 2H); 7.41(m, 2H); 7.64(dd, J=8.5, 1.9 Hz, 2H); 9.69(bb, 1H); 10.75(s, 1H). (DMSO-d6) |
| 25 | H | (CH₃)₂N— | 2 | H | 4-biphenyl | — | 184-186 | 3451, 3388, 2950, 2775, 1466, 1322, 1159, 1095, 763, 670, 591. | 2.08(s, 6H); 2.32(m, 2H); 2.64(m, 2H); 6.83(dd, J=8.6, 1.9 Hz, 1H); 7.08(d, J=2.0 Hz, 1H); 7.11(d, J=1.9 Hz, 1H); 7.17(d, J=8.6 Hz, 1H); 7.34-7.50(m, 3H); 7.66(d, J=7.5 Hz, 2H); 7.72(AB sys, J=8.6 Hz, 2H); 7.79(AB sys, J=8.6 Hz, 2H); 9.79(s, 1H); 10.75(s, 1H). (DMSO-d6). |
| 26 | H | (CH₃CH₂)₂N— | 2 | Et | 2-naphthyl | — | 49-50 | 3386, 2970, 2931, 1474, 1337, 1167, 1151, 1130, 1073, 661, 550 | 0.82(t, J=7.0 Hz, 6H); 0.98(t, J=7.0 Hz, 3H); 2.37(q, J=7.0 Hz, 4H); 2.49(m, 2H); 2.54(m, 2H); 3.66(q, J=7.1 Hz, 2H); 6.73(dd, J=8.61, 1.6 Hz, 1H); 6.98(s, 1H); 7.17(d, J=1.6 Hz, 1H); 7.26(d, J=8.61 Hz, 1H); 7.56-7.72(m, 3H); 7.99-8.11(m, 3H); 8.26(s, 1H); 10.97(s, 1H). (DMSO-d6). |
| 27 | H | morpholinyl | 2 | H | 5-chloro-2,3-dimethylbenzothiophene | — | 200-201 | 3366, 2951, 2816, 1460, 1421, 1319, 1283, 1157, 1114, 1078, 865, 651, 561 | 2.25(m, 6H); 2.27(s, 3H); 2.62(t, J=7.9 Hz, 2H); 3.52(m, 4H); 6.84(d, J=8.2 Hz, 1H); 7.06(s, 1H); 7.10(s, 1H); 7.20(d, J=8.6 Hz, 1H); 7.50(d, J=8.6 Hz, 1H); 7.92(s, 1H); 8.00(d, J=8.6 Hz, 1H); 10.13(s, 1H); 10.80(s, 1H). (DMSO-d6) |
| 28 | H | morpholinyl | 2 | H | 1-methylnaphthyl | — | 218-220 | 3389, 3152, 2916, 2819, 1466, 1313, 1157, 1129, 1108, 771, 587 | 2.30(m, 6H); 2.56(m, 2H); 3.56(m, 4H); 6.69(d, J=8.4 Hz, 1H); 6.93(s, 1H); 7.06(m, 2H); 7.48(t, J=7.3 Hz, 1H); 7.67(m, 2H); 8.02(m, 2H); 8.13(d, J=8.1 Hz, 1H); 8.78(d, J=8.1 Hz, 1H); 10.10(s, 1H); 10.68(s, 1H). (DMSO-d6) |
| 29 | H | (CH₃CH₂)₂N— | 2 | CH₃ | 2-naphthyl | — | 134-136 | 2968, 2930, 1488, 1329, 1159, 1131, 1074, 660, 550 | 0.98(t, J=7.1 Hz, 6H); 2.55(m, 6H); 2.70(m, 2H); 3.67(s, 3H); 6.84(s, 1H); 6.93(dd, J=8.6, 2 Hz, 1H); 7.10(d, J=8.7 Hz, 1H); 7.18(d, J=1.7 Hz, 1H); 7.26(s, 1H); 7.57(m, 2H); 7.67(dd, J=8.7, 1.8 Hz, 1H); 7.84(m, 3H); 8.27(d, J=1.7 Hz, 1H). (DMSO-d6) |
| 30 | H | (CH₃)₂N— | 1 | H | 5-chloro-2,3-dimethylbenzothiophene | — | 148-152 | 3398, 2930, 1467, 1158, 1113, 1079, 861, 803, 651, 561 | 1.89(m, 6H); 2.29(s, 3H); 2.48(s, 2H); 6.83(m, 1H); 7.18(m, 3H); 7.50(m, 1H); 7.91(m, 1H); 8.00(m, 1H); 10.13(b, 1H); 10.92(s, 1H). (DMSO-d6) |

-continued

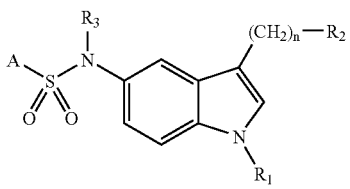

| Ex | R₁ | R₂ | n | R₃ | A | Salt | m.p. °C. | IR cm⁻¹ | ¹H-RMN (300 MHz), δ (solvent) |
|---|---|---|---|---|---|---|---|---|---|
| 31 | H | (CH₃CH₂CH₂)₂N— | 2 | H | 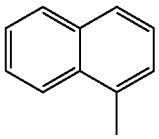 | — | 76-80 | 3399, 2959, 2931, 1466, 1159, 1132, 802, 770, 588 | 0.82(t, J=6.7 Hz, 6H); 1.34(q, J= 6.71 Hz, 4H); 2.31(m, 4H); 2.40(m, 2H); 2.52(m, 2H); 6.69(d, J=8.6 Hz, 1H); 7.04(m, 3H); 7.47(m, 1H); 7.66(m, 2H); 8.02(m, 2H); 8.11(d, J=8.1 Hz, 1H); 8.78(d, J=8.4 Hz, 1H); 10.12(s, 1H); 10.67(s, 1H). (DMSO-d6) |
| 32 | H | (CH₃CH₂CH₂)₂N— | 2 | H | 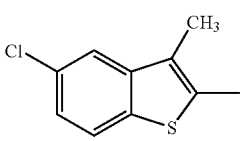 | — | 90-95 | 3406, 2959, 2932, 2872, 1466, 1157, 1079, 861, 652, 561 | 0.80(t, J=7.3 Hz, 6H); 1.31(q, J= 7.3 Hz, 4H); 2.26(m, 7H); 2.38(m, 2H); 2.56(m, 2H); 6.83(dd, J=8.4, 1.8 Hz, 1H); 7.08(s, 2H); 7.20(d, J=8.6 Hz, 1H); 7.50(dd, J=8.6, 2.0 Hz, 1H); 7.90(d, J=2.0 Hz, 1H); 7.99(d, J=8.6 Hz, 1H); 10.12(b, 1H); 10.79(s, 1H). (DMSO-d6) |
| 33 | H | (CH₃CH₂CH₂CH₂)₂N— | 2 | H | 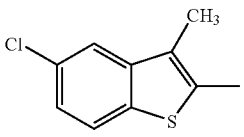 | — | 79-80 | 3398, 2956, 2930, 2870, 1466, 1158, 1080, 862, 801, 653, 562 | 0.84(t, J=6.8 Hz, 6H); 1.24(m, 8H); 2.26(s, 3H); 2.28(m, 4H); 2.39(m, 2H); 2.57(m, 2H); 6.82(dd, J=8.6, 1.9 Hz, 1H); 7.09(d, J=1.8 Hz, 2H); 7.18(d, J= 8.6 Hz, 1H); 7.50(dd, J=8.6, 1.9 Hz, 1H); 7.89(d, J=1.8 Hz, 1H); 7.98(d, J=8.6 Hz, 1H); 10.14(b, 1H); 10.78(s, 1H). (DMSO-d6) |
| 34 | H | (CH₃CH₂CH₂CH₂)₂N— | 2 | H | 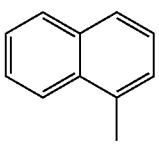 | — | 111-113 | 3291, 2955, 2926, 2870, 1327, 1158, 1136, 772, 676, 611, 585 | 0.86(t, J=7.0 Hz, 6H); 1.29(m, 8H); 2.35(m, 4H); 2.41(m, 2H); 2.53(m, 2H); 6.67(dd, J=8.5, 1.9 Hz, 1H); 7.09(m, 3H); 7.48(t, J= 7.9 Hz, 1H); 7.68(m, 2H); 8.01(s,, 1H); 8.04(s, 1H); 8.12(d, J=8.2 Hz, 1H); 8.78(d, J=8.2 Hz, 1H); 10.13(s, 1H); 10.67(s, 1H). (DMSO-d6) |
| 35 | H | (CH₃CH₂)₂N— | 2 | H | 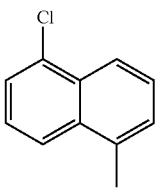 | — | 154-156 | 3402, 2978, 1471, 1285, 1162, 1135, 1018, 780, 629, 606 | 0.88(t, J=6.7 Hz, 6H); 2.41(m, 6H); 2.49(m, 2H); 6.71(d, J=8.1 Hz, 1H); 6.88(s, 1H); 7.07(m, 2H); 7.66(m, 2H); 7.84(d, J=7.0 Hz, 1H); 8.09(d, J=7.0 Hz, 1H); 8.41(d, J=8.2 Hz, 1H); 8.79(d, J= 8.6 Hz, 1H); 10.17(b, 1H); 10.71(s, 1H). (DMSO-d6) |
| 36 | H | (CH₃CH₂)₂N— | 2 | H | 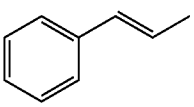 | — | 125-130 | 3404, 2972, 1473, 1319, 1142, 967, 745, 541 | 0.94(t, J=7.1 Hz, 6H); 2.50(q, J= 7.1 Hz, 4H); 2.59(m, 2H); 2.68(m, 2H); 6.94(dd, J=8.6, 1.8 Hz, 1H); 7.26(m, 8H); 7.59(m, 2H); 9.54(b, 1H); 10.77(s, 1H). (DMSO-d6) |
| 37 | H | 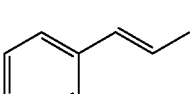 | 1 | H | 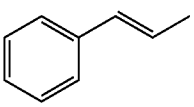 | — | 203 (desc) | 2809, 1340, 1150, 746, 542 | 2.06(s, 3H); 2.22(m, 6H); 3.36(m, 2H); 3.49(s, 2H); 6.95(dd, J=8.6, 1.8 Hz, 1H); 7.18(s, 2H); 7.24(m, 2H); 7.37(m, 3H); 7.45(d, J=1.8 Hz, 1H); 7.61(m, 2H); 9.53(s, 1H); 10.90(s, 1H). (DMSO-d6) |

-continued

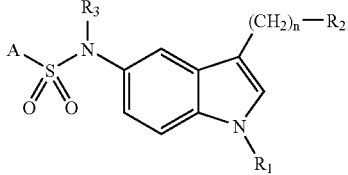

| Ex | R₁ | R₂ | n | R₃ | A | Salt | m.p. °C. | IR cm⁻¹ | ¹H-RMN (300 MHz), δ (solvent) |
|---|---|---|---|---|---|---|---|---|---|
| 38 | H | 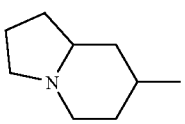 | 0 | H | 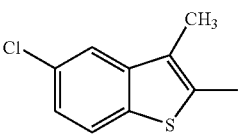 | — | 142-144 | 3413, 2929, 1157, 1113, 1080, 862, 651, 564 | 1.12(m, 3H); 1.81(m, 9H); 2.22(s, 3H); 2.93(m, 2H); 6.84(dd, J=8.5, 1.7 Hz, 1H); 6.99(s, 1H); 7.03(s, 1H); 7.20(d, J=8.6 Hz, 1H); 7.52(dd, J=8.6, 2.0 Hz, 1H); 7.90(d, J=1.7 Hz, 1H); 8.00(d, J=8.6 Hz, 1H); 10.01(b, 1H); 10.61(s, 1H). (DMSO-d6) |
| 39 | H | (CH₃CH₂)₂N— | 2 | H | 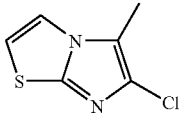 | — | 197-198 | 3338, 1466, 1270, 1237, 117, 986, 626 | 0.96(t, J=7.1 Hz, 6H); 2.53(m, 6H); 2.63(m, 2H); 6.78(dd, J=8.5, 1.6 Hz, 1H); 7.10(s, 2H); 7.18(d, J=8.6 Hz, 1H); 7.51(d, J=4.6 Hz, 1H); 7.80(d, J=4.6 Hz, 1H); 10.78(s, 1H). (DMSO-d6) |
| 40 | H | 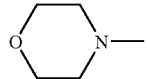 | 2 | H | 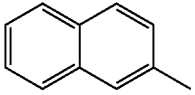 | — | 85-90 | 3399, 3257, 2920, 2855, 2814, 1460, 1330, 1157, 1131, 1113, 1074, 659, 551, 477 | 2.27(m, 6H); 2.61(t, J=7.9 Hz, 2H); 3.52(t, J=4.6 Hz, 4H); 6.82(dd, J=8.6, 2.0 Hz, 1H); 7.06(s, 1H); 7.07(s, 1H); 7.15(d, J=8.6 Hz, 1H); 7.61(m, 2H); 7.74(dd, J=8.8, 1.8 Hz, 1H); 7.96(d, J=8.1 Hz, 1H); 8.03(m, 2H); 8.27(s, 1H); 9.87(s, 1H); 10.74(s, 1H). (DMSO-d6) |
| 41 | H | 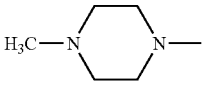 | 1 | H | 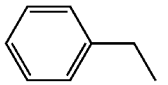 | — | 99-102 | 3398, 2934, 2806, 1458, 1331, 1284, 1153, 1127, 700, 542 | 2.11(s, 3H); 2.32(m, 6H); 3.35(m, 2H); 3.56(s, 2H); 4.29(s, 2H); 6.98(d, J=8.2 Hz, 1H); 7.29(m, 7H); 7.53(s, 1H); 9.40(s, 1H); 10.94(s, 1H). (DMSO-d6) |
| 42 | H | (CH₃CH₂)₂N— | 3 | H | 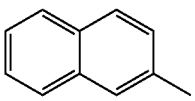 | — | 128-130 | 3259, 2973, 2939, 2827, 1468, 1332, 1159, 1131, 1075, 670, 555 | 0.86(t, J=7.0 Hz, 6H); 1.51(t, J=6.9 Hz, 2H); 2.27(t, J=6.9 Hz, 2H); 2.35(q, J=7.0 Hz, 4H); 2.46(m, 2H); 6.77(d, J=8.6 Hz, 1H); 7.00(s, 1H); 7.10(m, 2H); 7.60(m, 2H); 7.72(d, J=8.8 Hz, 1H); 7.95(d, J=7.9 Hz, 1H); 8.02(m, 2H); 8.26(s, 1H); 9.86(b, 1H); 10.67(s, 1H). (DMSO-d6) |
| 43 | H | (CH₃CH₂)₂N— | 3 | H | 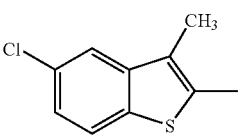 | — | 156-158 | 3247, 2969, 2938, 1467, 1340, 1159, 1113, 1080, 862, 666, 558 | 0.88(t, J=7.0 Hz, 6H); 1.52(m, 2H); 2.29(m, 5H); 2.37(q, J=7.0 Hz, 4H); 2.47(m, 2H); 6.81(dd, J=8.6, 1.5 Hz, 1H); 7.06(d, J=1.6 Hz, 1H); 7.12(d, J=1.5 Hz, 1H); 7.18(d, J=8.6 Hz, 1H); 7.51(dd, J=8.6, 2.0 Hz, 1H); ); 7.91(d, J=2.0 Hz, 1H); 7.99(d, J=8.6 Hz, 1H); 10.06(b, 1H); 10.76(s, 1H). (DMSO-d6) |
| 44 | H | 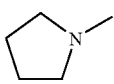 | 2 | H | 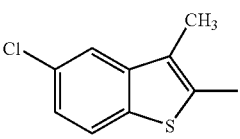 | — | 201-203 | 3386, 2929, 1466, 1157, 1106, 1080, 992, 861, 650, 564 | 1.62(m, 4H); 2.29(s, 3H); 2.30(m, 4H); 2.36(m, 2H); 2.63(m, 2H); 6.86(d, J=8.6 Hz, 1H); 7.05(s, 1H); 7.09(s, 1H); 7.21(dd, J=8.6, 2.2 Hz, 1H); 7.50(dd, J=8.7, 2.0 Hz, 1H); 7.92(s, 1H); 7.99(dd, J=8.7, 2.2 Hz, 1H); 10.10(b, 1H); 10.81(s, 1H). (DMSO-d6) |

-continued

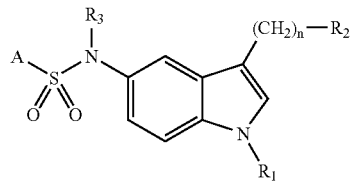

| Ex | R₁ | R₂ | n | R₃ | A | Salt | m.p. ° C. | IR cm⁻¹ | ¹H-RMN (300 MHz), δ (solvent) |
|---|---|---|---|---|---|---|---|---|---|
| 45 | H | N-methylpyrrolidinyl | 2 | H | 1-methylnaphthalene | — | 212–214 | 3354, 2964, 2812, 1466, 1201, 1157, 1124, 808, 773, 593 | 1.66(m, 4H); 2.36(m, 6H); 2.58(m, 2H); 6.71(d, J=8.6 Hz, 1H); 6.93(s, 1H); 7.02(s, 1H); 7.07(d, J=8.6 Hz, 1H); 7.48(m, 1H); 7.68(m, 2H); 8.02(dd, J=7.2, 1.2 Hz, 2H); 8.12(d, J=8.2 Hz, 1H); 8.79(d, J=8.6 Hz, 1H); 10.10(b, 1H); 10.68(s, 1H). (DMSO-d6) |
| 46 | H | N-methylpyrrolidinyl | 2 | H | 2-methylnaphthalene | — | 180–182 | 3375, 2968, 2821, 1467, 1323, 1313, 1146, 1139, 1131, 1079, 972, 654, 549 | 1.60(m, 4H); 2.26(m, 4H); 2.35(m, 2H); 2.61(m, 2H); 6.82(dd, J=8.6, 2.0 Hz, 1H); 7.05(m, 2H); 7.14(d, J=8.6 Hz, 1H); 7.61(m, 2H); 7.74(dd, J=8.6, 1.8 Hz, 1H); 7.95(d, J=7.9 Hz, 1H); 8.02(m, 2H); 8.27(s, 1H); 9.86(b, 1H); 10.72(s, 1H). (DMSO-d6) |
| 47 | H | (CH₃CH₂CH₂)₂N— | 2 | H | 2-methylnaphthalene | — | 58–64 (desc) | 3398, 3255, 2958, 2931, 2872, 1466, 1330, 1156, 1130, 1074; 659, 551 | 0.79(t, J=7.3 Hz, 6H); 1.31(q, J=7.3 Hz, 4H); 2.28(t, J=7.3 Hz, 4H); 2.42(m, 2H); 2.57(m, 2H); 6.80(dd, J=8.6, 1.7 Hz, 1H); 7.04(d, J=1.7 Hz, 1H); 7.12(m 2H); 7.60(m, 2H); 7.72(dd, J=8.6, 1.7 Hz, 1H); 7.98(m, 3H); 8.25(s, 1H); 9.87(b, 1H); 10.70(s, 1H). (DMSO-d6) |
| 48 | H | (CH₃)₂N— | 2 | H | 5-chloro-1-methylnaphthalene | — | 201–203 | 3369, 1473, 1161, 1125, 1017, 789, 619 | 2.06(s, 6H); 2.15(t, J=8.2 Hz, 2H); 2.52(t, J=8.2 Hz, 2H); 6.69(d, J=8.7 Hz, 1H); 6.85(s, 1H); 7.02(s, 1H); 7.08(d, J=8.7 Hz, 1H); 7.67(m, 2H); 7.84(d, J=7.3 Hz, 1H); 8.10(d, J=7.3 Hz, 1H); 8.41(d, J=8.4 Hz, 1H); 8.79(d, J=8.7 Hz, 1H); 10.15(b, 1H); 10.70(s, 1H). (DMSO-d6) |
| 49 | H | (CH₃)₂N— | 2 | H | 3-methylnaphthalene | — | 180–190 | 3399, 3255, 2943, 1466, 1330, 1156, 1131, 1075, 659, 550 | 2.03(s, 6H); 2.22(t, J=8.2 Hz, 2H); 2.58(t, J=8.2 Hz, 2H); 6.80(d, J=8.4 Hz, 1H); 7.04(s, 1H); 7.07(s, 1H); 7.13(d, J=8.6 Hz, 1H); 7.60(m, 2H); 7.74(d, J=8.6 Hz, 1H); 7.95(d, J=7.7 Hz, 1H); 8.02(m, 2H); 8.26(s, 1H); 9.86(b, 1H); 10.71(s, 1H). (DMSO-d6) |
| 50 | H | morpholinyl | 2 | H | 8-methylquinoline | — | 234–235 | 3400, 3279, 2913, 2852, 1464, 1420, 1315, 1163, 1118, 951, 592 | 2.29(m, 6H); 2.54(m, 2H); 3.57(m, 4H); 6.72(d, J=8.1 Hz, 1H); 7.01(m, 3H); 7.60(t, J=7.7 Hz, 1H); 7.74(d, J=8.4 Hz, 1H); 8.19(m, 2H); 8.52(d, J=8.4 Hz, 1H); 9.21(s, 1H); 9.44(s, 1H); 10.65(s, 1H). (DMSO-d6) |
| 51 | H | morpholinyl | 2 | H | 4-methylbiphenyl | — | 225–228 | 3340, 2857, 1479, 1324, 1153, 1116, 1094, 768, 670, 588 | 2.29(m, 6H); 2.66(m, 2H); 3.47(m, 4H); 6.84(d, J=8.6 Hz, 1H); 7.07(s, 1H); 7.09(s, 1H); 7.18(d, J=8.4 Hz, 1H); 7.45(m, 3H); 7.70(m, 4H); 7.79(m, 2H); 9.79(s, 1H); 10.77(s, 1H). (DMSO-d6) |

-continued

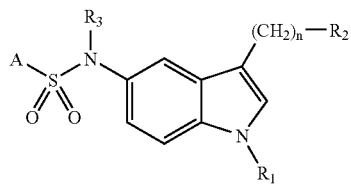

| Ex | R₁ | R₂ | n | R₃ | A | Salt | m.p. °C. | IR cm$^{-1}$ | $^1$H-RMN (300 MHz), δ (solvent) |
|----|----|----|---|----|---|------|----------|---------------|-----------------------------------|
| 52 | H | H₃C—N‿‿— | 2 | H | (2-naphthyl) | — | 129-131 | 3367, 2924, 2852, 2799, 1465, 1311, 1154, 1130, 1077, 666, 557 | 1.40-1.60(m, 4H); 1.83(m, 2H); 2.14(s, 3H); 2.36(m, 1H); 2.67(d, J=11.2 Hz, 2H); 6.78(d, J=8.4 Hz, 1H); 6.97(s, 1H); 7.00(s, 1H); 7.12(d, J=8.6 Hz, 1H); 7.50-7.68(m, 2H); 7.73(d, J=9.0 Hz, 1H); 8.00(m, 3H); 8.23(s, 1H); 9.78(b, 1H); 10.71(s, 1H). (DMSO-d6) |
| 53 | H | H₃C—N‿‿— | 2 | H | (5-chloro-1-naphthyl) | — | 246-249 | 3329, 2940, 2916, 1470, 1158, 1125, 1110, 1015, 791, 598 | 1.35-1.47(m, 4H); 1.86(m, 2H); 2.17(s, 3H); 2.28(m, 1H); 2.76(d, J=10.6 Hz, 2H); 6.68(d, J=8.8 Hz, 1H); 6.75(s, 1H); 6.94(s, 1H); 7.08(d, J=9.0 Hz, 1H); 7.60-7.73(m, 2H); 7.85(d, J=7.1 Hz, 1H); 8.06(d, J=7.1 Hz, 1H); 8.40(d, J=7.9 Hz, 1H); 8.79(d, J=9.0 Hz, 1H); 10.20(b, 1H); 10.68(s, 1H). (DMSO-d6) |

BIOLOGICAL ASSAYS

Binding with Serotonin Receptor 5HT$_6$

Cell membranes of HEK-293 cells expressing the 5HT$_6$ human recombinant receptor were supplied by Receptor Biology. In said membranes the receptor concentration is 2.18 pmol/mg protein and the protein concentration is 9.17 mg/ml. The experimental protocol follows the method of B. L. Roth et al. [B. L. Roth, S. C. Craigo, M. S. Choudhary, A. Uluer, F. J. Monsma, Y. Shen, H. Y. Meltzer, D. R. Sibley: Binding of Typical and Atypical Antipsychotic Agents to 5-Hydroxytryptamine-6 and Hydroxytryptamine-7 Receptors. *The Journal of Pharmacology and Experimental Therapeutics*, 1994, 268, 1403] with slight changes. The commercial membrane is diluted (1:40 dilution) with the binding buffer: 50 mM Tris-HCl, 10 mM MgCl$_2$, 0.5 mM EDTA (pH 7.4): The radioligand used is [$^3$H]-LSD at a concentration of 2.7 nM with a final volume of 200 μl. incubation is initiated by adding 100 μl of membrane suspension, (≈22.9 μg membrane protein), and is prolonged for 60 minutes at a temperature of 37° C. The incubation is ended by fast filtration in a Brandel Cell Harvester through fiber glass filters made by Schleicher & Schuell GF 3362 pretreated with a solution of polyethylenimine at 0.5%. The filters are washed three times with three milliliters of buffer Tris-HCl 50 mM pH 7.4. The filters are transferred to flasks and 5 ml of Ecoscint H liquid scintillation cocktail are added to each flask. The flasks are allowed to reach equilibrium for several hours before counting with a Wallac Winspectral 1414 scintillation counter. Non-specific binding is determined in the presence of 100 μM of serotonin. Tests were made in triplicate. The inhibition constants (K$_i$, nM) were calculated by non-linear regression analysis using the program EBDA/LIGAND [Munson and Rodbard, *Analytical Biochemistry*, 1980, 107, 220]. The following table shows results indicative of binding for some of the compounds object of the present invention.

TABLE

| Example | % Inhibition 10$^{-6}$ M | K$_i$ (nM) |
|---------|--------------------------|------------|
| 1 | 98.1 ± 4.0 | 0.28 |
| 3 | 96.6 ± 5.2 | 3.5 |
| 4 | 96.2 ± 0.6 | 9.3 |
| 5 | 101.2 ± 0.1 | 1.0 |
| 6 | 97.6 ± 1.8 | 8.7 |
| 7 | 103.0 ± 7.9 | 0.13 |
| 8 | 94.5 ± 7.0 | 0.76 |
| 9 | 96.8 ± 3.7 | 2.2 |
| 11 | 101.3 | 0.98 |
| 13 | 98.3 | 4.7 |
| 14 | 95.7 ± 3.4 | 24.3 |
| 15 | 97.4 ± 0.8 | 6.8 |
| 16 | 94.4 ± 8.6 | 21.2 |
| 17 | 102.0 | 5.3 |

The daily doses in human medicine are between 1 milligram and 500 milligrams of product, which can be given in one or more administrations. The compositions are prepared in forms compatible with the administration means used, such as sugar-coated pills, tablets, capsules, suppositories, solutions or suspensions. These compositions are prepared by known methods and comprise between 1 and 60% by weight of the active principle (compound with the general formula 1) and 40 to 99% by weight of a suitable pharmaceutical vehicle compatible with the active principle and the physical form of the composition used. By say of example, the formula of a tablet containing a product of the invention is shown.

| Example of formula per tablet: | |
|--------------------------------|---|
| Example 1 | 5 mg |
| Lactose | 60 mg |

-continued

Example of formula per tablet:

| | |
|---|---|
| Crystalline cellulose | 25 mg |
| K 90 Povidone | 5 mg |
| Pregelatinised starch | 3 mg |
| Colloidal silicon dioxide | 1 mg |
| Magnesium stearate | 1 mg |
| Total weight per tablet | 100 mg |

What is claimed is:

1. A compound derived of sulphonamide with the general formula (1)

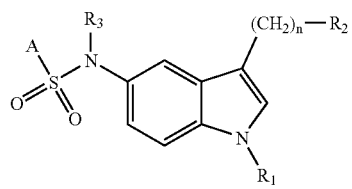

(I)

wherein A represents a substituent selected from among:
A bicyclic heteroaromatic ring containing 1 to 3 heteroatoms selected from among oxygen, nitrogen and sulphur, optionally substituted by 1 or 2 halogen atoms or by a $C_1$-$C_4$ alkyl radical;
$R_1$ represents hydrogen, a $C_1$-$C_4$ alkyl radical or a benzyl radical;
n represents 0, 1, 2, 3 or 4;
$R_2$ represents —$NR_4R_5$ or a group with formula:

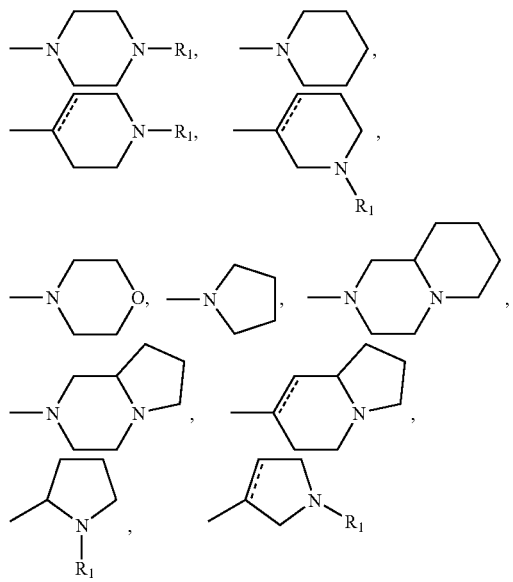

Wherein the dotted line represents an optional chemical bond; and
$R_3$, $R_4$ and $R_5$ independently represent hydrogen or a $C_1$-$C_4$ alkyl;
with the condition that when m=0, A is a substituted phenyl; or one of its physiologically acceptable salts.

2. Pharmaceutical compositions, characterized in that they contain, in addition to the pharmaceutically acceptable excipients, at least one compound with the general formula (I) or one of its physiologically acceptable salts, according to claim 1.

3. A pharmaceutical composition comprising a compound derived of sulphonamide with the general formula (1)

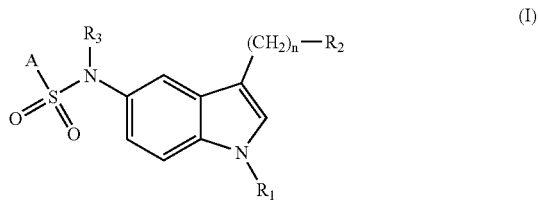

(I)

wherein A represents a substituent selected from among:
A bicyclic heteroaromatic ring containing 1 to 3 heteroatoms selected from among oxygen, nitrogen and sulphur, optionally substituted by 1 or 2 halogen atoms or by a $C_1$-$C_4$ alkyl radical;
$R_1$ represents hydrogen, a $C_1$-$C_4$ alkyl radical or a benzyl radical;
n represents 0, 1, 2, 3 or 4;
$R_2$ represents —$NR_4R_5$ or a group with formula:

(II)

Wherein the dotted line represents an optional chemical bond; and
$R_3$, $R_4$ and $R_5$ independently represent hydrogen or a $C_1$-$C_4$ alkyl;
or one of its physiologically acceptable salts.

4. A compound, according to claim 1, selected from among the following group:

[1] N-[3-(2-diethylaminoethyl)-1H-indol-5-yl]-5-chloro-3-methylbenzo[b]thiophene-2-sulphonamide;

[2] N-[3-(2-dimethylaminoethyl)-1H-indol-5-yl]-5-chloro-3-methylbenzo [b]thiophene-2-sulphonamide;

[3] N-[3-(2-dimethylamino-ethyl)-1H-indol-5-yl]-6-chloroimidazo[2,1-b]thiazol-5-sulphonamide;

[4] N-[3-(1-methylpiperidin-4-yl)-1H-indol-5-yl]-5-chloro-3-methylbenzo[b]thiophene-2-suiphonamide;

[5] N-[3-(1-methylpiperidin-4-yl)-1H-indol-5-yl]-5-chloro-3-methylbenzo[b]thiophene-2-sulphonamide hydrochloride;

[6] N-[3-(1-methylpiperidin-4-yl)-1H-indol-5-yl]quinoline-8-sulphonamide;

[7] N-[3-(4-methylpiperazin-1-yl)methyl-1H-indol-5-yl]-5-chloro-3-methylbenzo[b]thiophene-2-sulphonamide;

[8] N-[3-(2-dimethylaminoethyl)-1H-indol-5-yl]-2,1,3-benzothiadiazol-4-sulphonamide;

[9] N-[3-(2-dimethylaminoethyl)-1H-indol-5-yl]quinoline-8-sulphonamide;

[10] N-[3-[2-(morpholin-4-yl)ethyl]-1H-indol-5-yl]-5-chloro-3-methylbenzo[b]thiophene-2-sulphonamide;

[11] N-[3-dimethylaminomethyl-1-)-1H-indol-5-yl]-5-chloro-3-methylbenzo[b]thiophene-sulphonamide;

[12] N-[3-(2-dipropylaminoethyl)-1H-indol-5-yl]-5-chloro-3-methylbenzo[b]thiophene-sulphonamide;
[13] N-[3-(2-dibutylaminoethyl)-1)-1H-indol-5-yl]-5-chloro-3-methylbenzo[b]thiophenesulphonamide;
[14] N-[3-(octahydroindolizin-7-yl)-1H-indol-5-yl]5-chloro-3 methylbenzo [b]thiophene-2-sulphonamide;
[15] N-[3-(2-diethylaminoethyl)-1H-indol-5-yl]-6-chloroimidazo[2,1-b]thiazol-5-sulphonamide;
[16] N-[3-(3-diethylaminopropyl)-1H-indol-5-yl]-5-chloro-3-methylbenzo[b]thiophene-2-sulphonamide;
[17] N-[3-[2-(pyrrolidin-1-yl)ethyl]-1H-indol-5-yl]-5-chloro-3-methylbenzo[b]thiophene-2-sulphonamide;
[18] N-[3-[2-(morpholin-4-yl)ethyl]-1H-indol-5-yl] quinoline-8-sulphonamide.

\* \* \* \* \*